United States Patent [19]

Massino

[11] Patent Number: 5,567,160

[45] Date of Patent: Oct. 22, 1996

[54] AUTOINJECTOR TRAINING DEVICE

[75] Inventor: Frank Massino, Rockville, Md.

[73] Assignee: Survival Technology, Inc., Rockville, Md.

[21] Appl. No.: 548,858

[22] Filed: Oct. 26, 1995

[51] Int. Cl.$^6$ ................................................. G09B 23/28
[52] U.S. Cl. .......................................... 434/262; 604/135
[58] Field of Search .................................. 434/262, 272; 604/131, 135, 134

[56] References Cited

U.S. PATENT DOCUMENTS

| | | |
|---|---|---|
| 3,426,448 | 2/1969 | Sarnoff . |
| 3,795,061 | 3/1974 | Sarnoff et al. . |
| 4,640,686 | 2/1987 | Dalling et al. . |
| 4,717,383 | 1/1988 | Phillips et al. ........................ 604/135 |
| 5,037,306 | 8/1991 | van Schoonhoven ................. 604/135 |
| 5,071,353 | 12/1991 | van der Wal . |
| 5,085,642 | 2/1992 | Sarnoff ................................. 604/135 |
| 5,320,609 | 6/1994 | Haber et al. .......................... 604/135 |
| 5,358,489 | 10/1994 | Wyrick ................................ 604/135 |
| 5,391,151 | 2/1995 | Wilmot ................................ 604/135 |
| 5,425,715 | 6/1995 | Dalling et al. ....................... 604/135 |

*Primary Examiner*—Paul J. Hirsch
*Attorney, Agent, or Firm*—Cushman Darby & Cushman

[57] ABSTRACT

An automatic injector training device comprises an outer structure having i) a rearward end, ii) a forward end arranged to be engaged with an injection site of the user, and iii) an intermediate portion. A manually movable actuating member is movable between a storage position and an activated position by being manually depressed by the user. A prod member is movable within the outer structure between a retracted position and an outwardly extending position when the actuating member is manually moved between the storage position to the activated position. A spring member is disposed within the outer structure and arranged so as to move the prod member from the outwardly extending position to the retracted position when the actuating member is moved from the activated position to the storage position. The actuating member is disposed so that manual movement thereof from the storage position to the activated position moves the prod member against the bias of the spring member so that the forward end of the prod member is moved to extend outwardly from the forward end of the outer structure. Releasable locking elements are disposed within the outer structure and retain the prod member in the outwardly extending position when the actuating member is moved to the activated position and permit the prod member to be moved to the retracted position when the actuating member is moved to the storage position. A safety member is movable between a safety position wherein the safety member prevents manual movement of the actuating member and a non-safety position which permits the actuating member to be manually moved between the activated position and the storage position.

2 Claims, 4 Drawing Sheets

AUTOINJECTOR TRAINING DEVICE

This invention relates to automatic injectors and more particularly to training devices for training individuals to use automatic injectors.

An automatic injector is a well known device for enabling an individual to self-administer a dosage of a liquid medicament. An advantage of automatic injectors is that they contain a measured dosage of a liquid medicament in a sealed sterile condition capable of storage in such condition for an extensive period of non-use, during which period immediate injection of the stored dosage may be accomplished at any time under the most severe emergency conditions. For example, automatic injectors have heretofore been manufactured and sold containing nerve gas antidotes for use under chemical warfare conditions. In addition, units of this type have been proposed for use in administering antiarrhythmic medicaments under emergency conditions relating to heart attack medical situations. As another example, injection devices of this type have been marketed containing a dosage of epinephrine as an antidote for counteracting severe allergic reactions, such as to bee stings and the like.

An automatic injector includes a stressed spring assembly, which when released, causes a hypodermic needle to project outwardly from the injector housing and to automatically dispense the stored liquid medicament through the needle. It can be appreciated that it is important that the user not hesitate to inject himself, either for fear of using the device or for lack of knowledge of proper use of the device at the critical moment when injection is required. It can also be appreciated that it is impractical for individuals to train themselves to use automatic injectors by repeatedly injecting themselves with a hypodermic needle. Thus, various training devices have been developed which enable a potential automatic injector user to become acquainted with the use thereof prior to the critical moment. Training devices of the type herein contemplated are known. Examples of known training devices are disclosed in U.S. Pat. Nos. 5,071,353, 5,037,306, 4,640,686, 3,795,061, and 3,426,448.

From a utility standpoint, a training device should be made to closely simulate the action of the automatic injector. The training device should also be capable of repeated use and also be capable of being made ready for reuse very easily. From a commercial standpoint, training devices should be made as inexpensively as possible.

While the aforementioned U.S. Patents relating to training devices have been effective in simulating the action of the automatic injector, they have not been made to be very user-friendly in that they each require some awkward procedure to recock the training device for reuse. For example, in the aforementioned U.S. Pat. Nos. 5,071,353, and 3,795,061 an auxiliary recocking tool must be used. In U.S. Pat. Nos. 3,426,448 and 5,037,306, a manual manipulation of the device is required before the prod member (which is a blunt elongate member that outwardly projects from the forward end of the training device housing to simulate the outwardly projecting hypodermic needle) itself must be physically forced back into the body of the training device, for example, by being thrust against a surface. In U.S. Pat. No. 4,640,686, no prod member is provided, and the training device must be reset or recocked by placing a safety pin element on a horizontal surface and then moving the training device downwardly onto the safety pin element until an opening in the training device fully receives the pin.

It is an object of the present invention to provide an injection training device that is relatively inexpensive to manufacture and simpler to use than those training devices known in the prior art. In accordance with the object of the invention, there is provided an automatic injector training device with an outer structure having i) a rearward end, ii) a forward end arranged to be engaged with an injection site of the user, and iii) an intermediate generally cylindrical portion disposed between the forward and rearward ends and constructed and arranged to be manually gripped by the user. A manually movable actuating member extends outwardly from the rearward end of the outer structure and is adapted to be manually engaged and depressed by the user while the intermediate portion is being gripped. The actuating member is movable between a storage position and an activated position by being manually depressed by the user. A prod member is movable within the outer structure between a retracted position wherein a forward portion thereof is disposed retracted within the outer structure and an outwardly extending position wherein the forward portion thereof extends outwardly from the forward end of the outer structure. The prod member is movable from the retracted position to the outwardly extending position when the actuating member is manually moved from the storage position to the activated position and is movable from the outwardly extending position to the retracted position when the actuating member is manually moved from the activated position to the storage position. A spring member is disposed within the outer structure and arranged so as to tend to bias the prod member rearwardly within the outer structure to thus move the prod member from the outwardly extending position to the retracted position when the actuating member is moved from the activated position to the storage position. The actuating member is disposed so that manual movement thereof from the storage position to the activated position moves the prod member against the bias of the spring member so that the forward end of the prod member is moved to extend outwardly from the forward end of the outer structure. Releasable locking elements are disposed within the outer structure and are constructed and arranged to retain the prod member in the outwardly extending position when the actuating member is moved from the storage position to the activated position and to permit the prod member to be moved by the spring member from the outwardly extending position to the retracted position when the actuating member is moved from the activated position to the storage position. A safety member is constructed and arranged to be movable between a safety position wherein the safety member prevents manual movement of the actuating member and a non-safety position which permits the actuating member to be manually moved between the activated position and the storage position.

These and other objects of the present invention will become more apparent during the course of the following detailed description and appended claims. The invention may best be understood with reference to the accompanying drawings wherein an illustrative embodiment is shown.

DETAILED DESCRIPTION OF THE DRAWINGS

Figure 1:
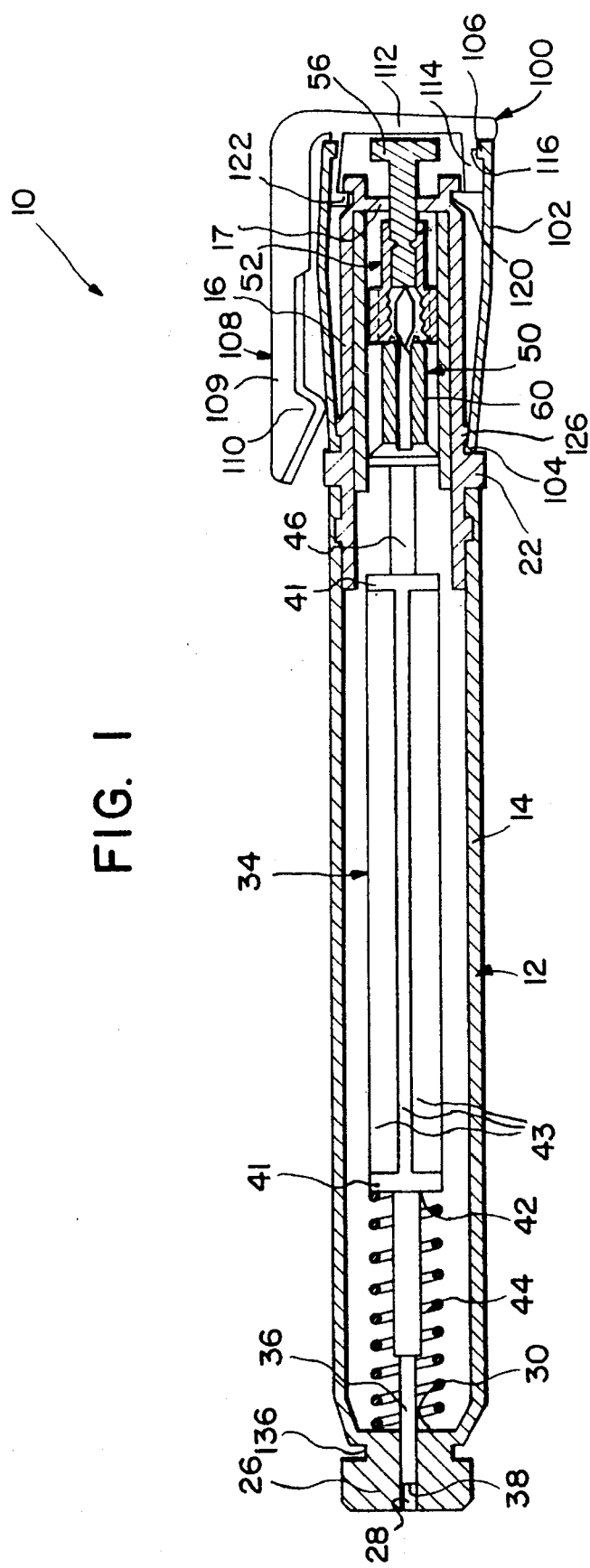
FIG. 1 is a longitudinal sectional view showing the automatic injector training device in accordance with the principles of the present invention.
Figure 2:
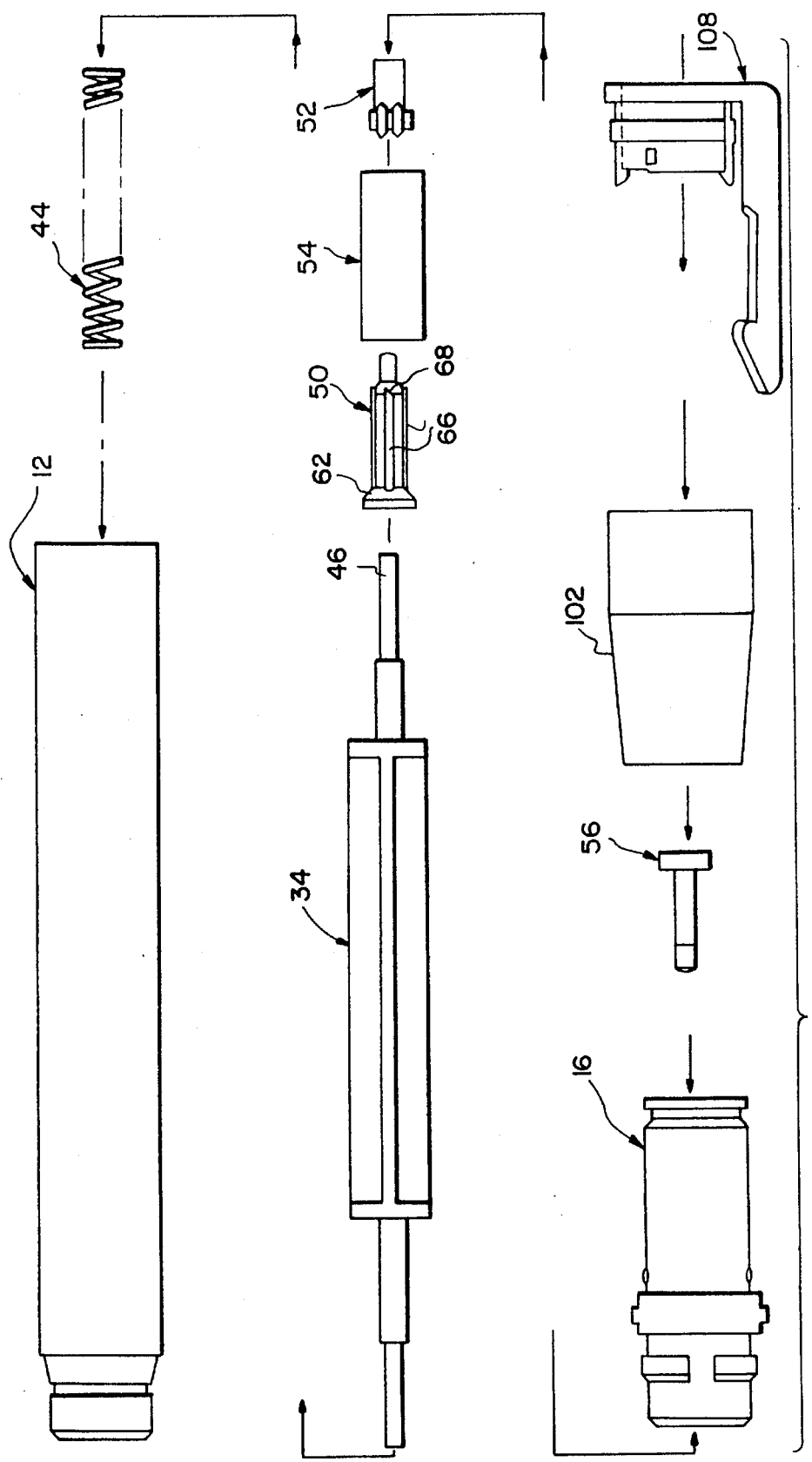
FIG. 2 is an exploded view showing the automatic injector training device in accordance with the principles of the present invention.

Referring more particularly to the drawings, the present invention will now be described in conjunction with FIGS. 1 and 2. There is shown in FIGS. 1 and 2 an automatic injector training device, generally indicated at 10, in accordance with the principles of the present invention.

As shown, the training device 10 has an elongate, tubular main housing or outer structure, generally indicated at 12. The outer structure basically comprises two portions, including a forward housing member 14, and a rearward housing member 16, each preferably formed from a molded plastic material. The forward and rearward housing members 14, 16, are substantially tubular in form, and are joined to one another by telescopically inserting the forward portion of the rearward housing member 16 into the rearward portion of the forward housing member 14. More particularly, slightly spaced from the rearward end of the forward housing member 14 is an annular groove 18 formed in the interior surface thereof. The forward portion of the rearward housing has an annular flange 20, slightly spaced from the forward end thereof and radially extending from the exterior surface thereof. The flange 20 is received within groove 18 to secure the rearward housing member 16 to the forward housing member 14. The rearward housing member 16 has an additional annular flange 22 extending radially outwardly from the outer surface thereof, and spaced slightly rearwardly from the flange 20. Flange 22 has a greater outer diameter than the flange 20, and has a forwardly facing surface 24 that serves as a stop for preventing the rearward end of the forward housing member 14 from extending rearwardly therebeyond. As also shown, the rearward housing member 16 has an inwardly extending annular flange 17, with a central aperture which can receive the stem of a manually engageable member 56.

The forward end of the forward housing member 14 has a radially inwardly extending guide portion 26 having a longitudinally extending central aperture 28 therethrough. The guide portion 26 has a rearwardly facing annular surface 30 surrounding the central aperture 28.

Disposed within the outer structure 12 is a generally elongate prod member 34. The prod member 34 is preferably made entirely out of a molded plastic material, and has a relatively narrowed diameter forward portion 36 thereof received within the central aperture 28 of the guide portion 26. In the position shown in FIG. 1, it can be seen that the prod member 34 is in a retracted position, wherein the entire prod member 34, including the forwardmost tip 38 thereof, is fully contained within the outer structure 12. The prod member 34 has an intermediate portion 40, which has disk-like forward and rearward portions 41, and four circumferentially spaced, longitudinal ribs 43 extending therebetween. The intermediate portion 40 has a greater diameter than the forward portion 36, and the forwardly disposed disk portion 41 presents a forwardly facing annular surface 42. A coil spring member 44 (preferably metallic) is disposed within the forward housing member 14 in surrounding relation with respect to the forward portion 36 of prod member 34. The coil spring 44 is compressed between the rearwardly facing surface 30 of the forward housing member 14 and the forwardly facing surface 42 of the forward disk portion 41. The slight compression of coil spring 44 normally retains the prod member 34 in the aforesaid retracted position within the outer structure 12.

The prod member 34 has a rearward portion 46, which cooperates with an actuating assembly 48. The actuating assembly 48 is best represented in FIG. 3, and can be seen to include a rotatable member 50, an actuating member 52, a track member 54, the previously mentioned manually engageable member 56, and may also be considered to include the rearward housing 16.

Various components of the actuating assembly 48, such as the rotatable member 50 and actuating member 52, are substantially identical to the structure utilized in a retractable ball-point pen. In fact, it is contemplated that because such components are made in bulk quantities, they can be purchased as a mass-produced, off-the-shelf components for incorporation into the training device of the present invention. As a result, the manufacturing costs of the training device of the present invention can be significantly reduced. The actuating assembly 48 will now be described in greater detail.

Figure 3:
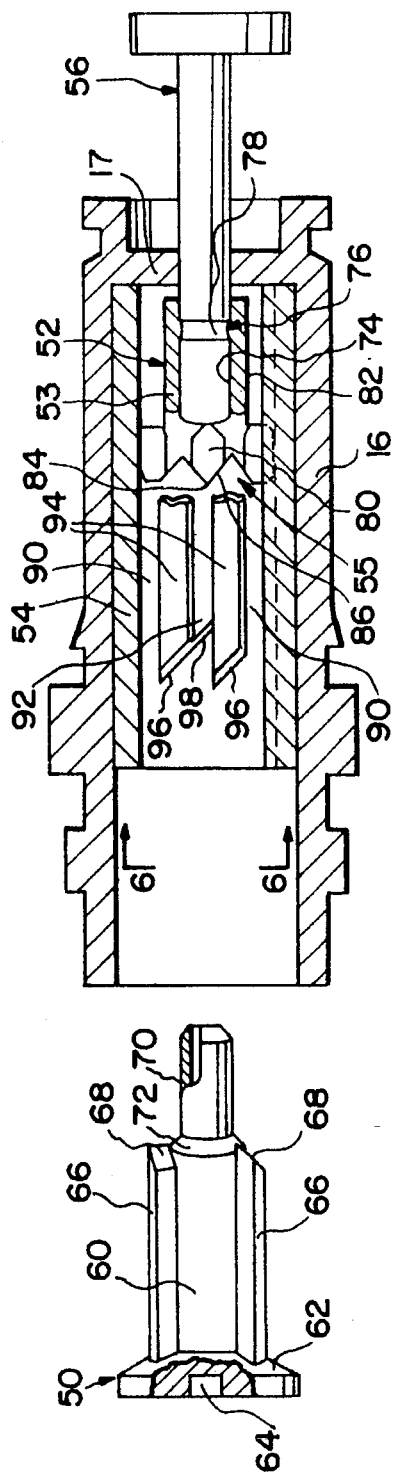
FIG. 3 is an enlarged view, partly in section, of the actuating assembly of the training device in accordance with the principles of the present invention.

As shown in FIGS. 1 and 2, and best shown in FIG. 3, the rotatable member 50 has a main cylindrical portion 60, and frusto-conical portion 62 formed at the forward end of cylindrical portion 60 and extending radially outwardly from the exterior surface of cylindrical portion 60. The frusto-conical portion 62 has a hollowed central portion 64, which is adapted to receive the rearward portion 46 of the prod member 34. Disposed on the exterior surface of cylindrical portion 60 is a plurality (preferably three) of circumferentially spaced, longitudinally extending ribs 66 each having sloped end faces 68 as shown. The rotatable member 50 further has a cylindrical rearward portion 70, with an outer diameter less than the outer diameter of cylindrical portion 60. A tapered frustum 72 connects the rearward cylindrical portion 70 with the main cylindrical portion 60.

Figure 5:
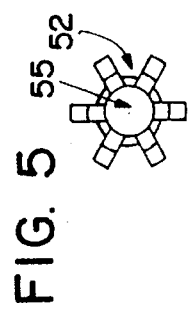
FIG. 5 is a bottom plan view showing the actuating member of the actuating assembly in accordance with the principles of the present invention.
Figure 4:
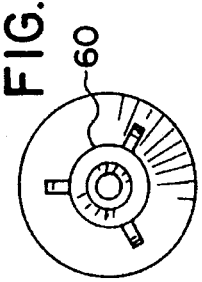
FIG. 4 is a top plan view showing the rotatable member of the actuating assembly in accordance with the principles of the present invention.
Figure 6:
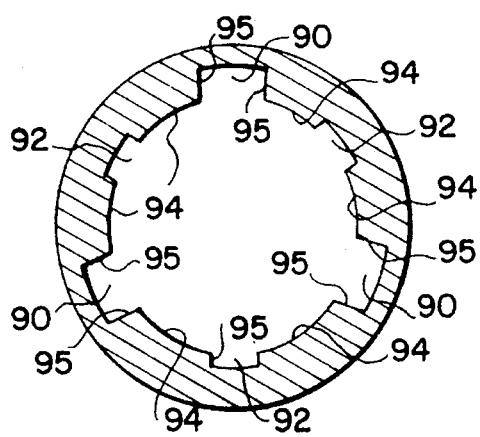
FIG. 6 is a transverse sectional view showing the tubular track member of the training device in accordance with the principles of the present invention.

The actuating member 52 has a main tubular portion 53 having a forward opening 55 (see FIG. 5) that loosely receives the rearward portion 70 of rotatable member 50. The rearward opening of rotatable member 50 securely receiving the forward end of the manually engageable member 56 as shown. Preferably, the interior surface 74 of the actuating member 52 has an annular ridge 76 extending radially inwardly at a position slightly spaced from the rearward end of the actuating member 52. The manually engageable member 56 has an annular groove 78 at a position slightly spaced from the forward end thereof. The groove 78 receives the annular ridge 76 so that the manually engageable member 56 is fixed to the actuating member 52. The actuating member 52 has a plurality (e.g., six) hexagonally-shaped engagement members 80 raised from the exterior surface 82 of the main tubular portion 53. The engagement members 80 are circumferentially spaced about the exterior surface 82 of the actuating member 52, towards the forward end thereof. The hexagonal engagement members 80 are arranged such that a forwardmost vertex 84 of each faces forwardly within the training device. A pair of slanting faces 86 extends rearwardly and circumferentially from each vertex 84.

As can be best appreciated from FIGS. 3, and 6–8, the track member 54 comprises a plurality of circumferentially spaced, longitudinally extending grooves formed in a cylindrical interior surface thereof. The grooves within the track member 54 are formed as alternating deep grooves 90 and shallow grooves 92, preferably six of each. Disposed between each groove is a longitudinally extending ledge 94, terminating at its forward end in a radially extending, slanted surface 96 as shown. It should be appreciated that shallow grooves 92 can also be considered as being longitudinally extending ledges, as they are slightly raised with respect to the deep grooves 90. In this regard, the shallow grooves or ledges 92 each terminate at their forward ends in circumferentially and rearwardly extending, sloped surfaces 98 as shown.

Figure 7:
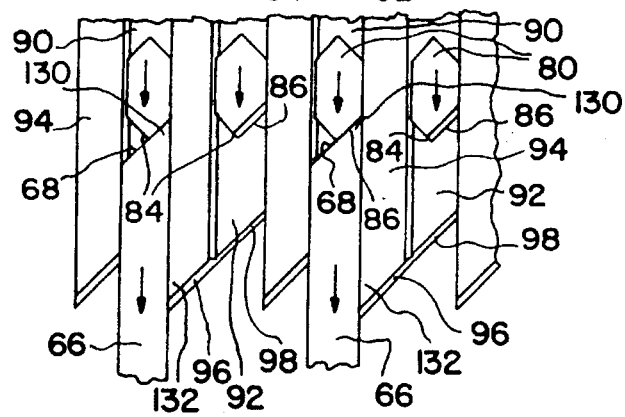
FIGS. 7 and 8 are schematic views showing various portions of the rotatable member, actuating member, and tubular track member that effectuate operation of the actuating assembly in accordance with the principles of the present invention.
Figure 8:
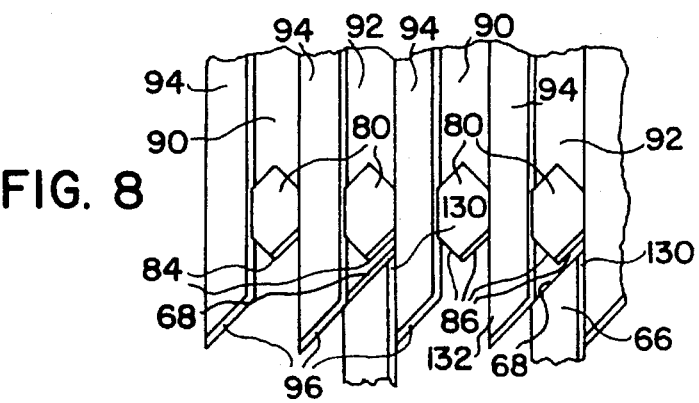
Figure 9:
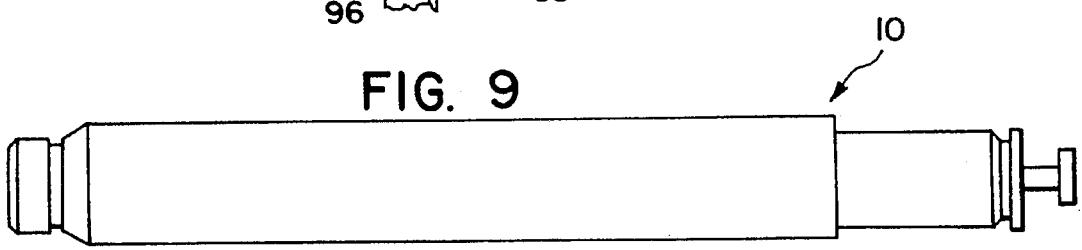
FIGS. 9 and 10 are longitudinal side views showing the training device in accordance with the principles of the present invention in different operating positions.

As can be appreciated from FIGS. 7 and 8, the hexagonal engagement members 80 have a radial dimension that enables them to slidably fit within both shallow grooves 92 and deep grooves 90. On the other hand, the ribs 66 of the rotatable member 50 have a radial dimension that is spaced from the central axis to a greater extent than that which would permit them to ride over sloped face 98 and be received within shallow grooves 92. However, the ribs 66 can readily slide within the deep grooves 90.

A removable safety cap member 100 is normally telescopically fitted over the rearward end of the device when the device is in the storage position. The safety cap member 100 includes a tubular member 102, which has a forwardly converging frusto-conical section that terminates in a forward interior flange 104 and a rearward, generally cylindrical section which terminates in a rearward interior flange 106.

The cap member 100 also includes a clip member, generally indicated at 108. As shown, the clip member 108 includes an elongated clip 109 having a forward end formed with a protrusion 110, which extends radially inwardly. Formed integrally with the rearward end of the clip 108 is a mounting section, which includes a circular rearward wall portion 112. A cylindrical wall portion 114 extends forwardly from the circular wall portion 112 and includes an annular groove 116 which is adapted to receive the rearward flange 106 of the tubular member 102 so that the clip member 108 and tubular member 102 can be secured to one another. The rearward end of rearward housing member 16 has an exterior annular groove 120, and the forwardmost end of the cylindrical wall 114 of the safety cap member 100 has at least one radially inwardly extending projection 122, which snaps into the annular groove 120 so as to secure the safety cap member 100 to the rearward housing member 16. In addition, the rearward housing member 16 has a plurality of circumferentially spaced, radially outwardly extending ridges 126 disposed slightly behind the annular flange 22. The flange 104 of the safety cap member 100 is retained between the flange 22 and the ridges 126 to further secure the safety cap member 100 to the rearward housing 16.

The safety cap member 100 is shown in a safety position in FIG. 1 wherein it is secured to the rearward housing 16 and covers the manually engageable member 56 so as to prevent manual engagement and movement of the manually engageable member 56. The cap 100 can be removed from the rearward housing 16 simply by grasping the exterior of the forward housing 14 with one hand and pulling the safety cap member 100 rearwardly so that the flange 104 rides rearwardly over the ridges 126 and so that the projection 122 is pulled out of the annular groove 120. After the safety cap 100 is removed, it is considered to be in a non-safety position, wherein the manually engageable member 56 can be accessed.

After the safety cap member 100 is removed, the training device can be actuated. More specifically, the user utilizes the device by grasping the intermediate cylindrical portion of the outer structure 12 in the palm and four fingers, and places the forwardmost end of the forward housing 14 into contact with an injection site, such as the thigh or arm. Next, the user depresses the rearwardly extending manually engageable member 56 (e.g., with the thumb) inwardly with respect to the rearward housing 16 so as to move the engageable member 56 from a storage position to an activated position. Such movement causes forward movement of the actuating member 52 so that the hexagonal engagement members 80 ride forwardly within the shallow and deep grooves 90. During such movement, as shown in FIG. 7, one of the slanting faces 86 of alternating engagement members 80 engages the rear sloping end face 68 of one of the ribs 66. More specifically, when the training device is in the inactivated or storage position (see FIG. 1), the ribs 66 are received within the alternate deep grooves 90 of the tubular track member 54 (see FIG. 7). When the manually engageable member 56 is depressed, it causes one of the slanting faces 86 of alternate engagement members 88 to engage the mating slanting end faces 68 and thus forces the ribs 66 forwardly out of the deep grooves 90. As a result, the rotatable member 50 drives the prod member 34 forwardly within the forward housing member 14 so that the forward end 38 of the prod member projects outwardly through the central opening 28 in the forward end of the forward housing member 14 against the spring bias of coil spring 44.

From FIG. 7, it can be appreciated that the engagement between the sloping faces 86 with the sloping faces 68 not only drives the ribs forwardly within the rearward housing, but also tends to exert a force on the ribs in a rotational direction about the longitudinal axis of the device. More specifically, in the schematic representation of FIG. 7, it can be appreciated that the driving force of the engagement members 80 against the ribs 66 tends to urge the ribs 66 towards the right, against one of the side surfaces 95 of the surrounding ledges 94. Thus, when the rearward tip 130 of the ribs 66 reaches the forwardmost tip 132 of the ledges 94, the ribs 66 are permitted to move to the right and ride over the forwardmost tip 132 of the ledges 94. Subsequently, the surfaces 68 of ribs 66 are permitted to slide rearwardly on slanted faces 96 of the ledges 94 until the slide onto sloped faces 98 of the shallow grooves 92. Thus, rotation of rotatable member 50 is accomplished in the transition from FIG. 7, which shows the retracted prod condition, to FIG. 8, which shows the extended prod condition.

Figure 10:
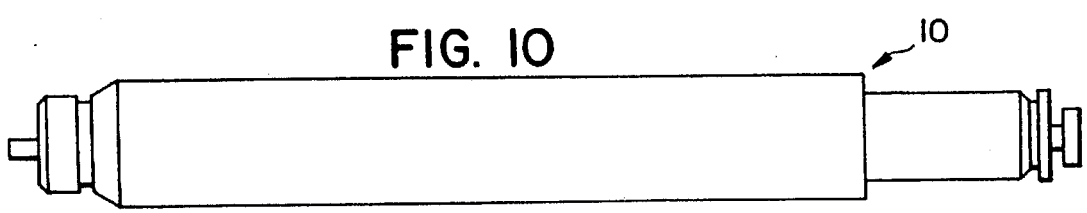

As best shown in FIG. 8, because the ribs 66 are of a radius that is greater than that which would permit such ribs to be received within shallow grooves 92, the end faces 68 of ribs 66 come to rest upon the sloped faces 98 of the grooves 92. Thus, the rotatable member 50 is releasably retained in a relatively forwardly disposed position relative to the position in which it assumes when its ribs 66 can be received within deep grooves 90. Because the prod member 34 is similarly retained in a relatively forward position, the forward portion 36 of the prod member is retained in a projecting or extended position from the forward end of the training device. The effect of the manual movement of the manually engageable member 56 from the storage position to the activated position in causing the forward projection of the forward portion 36 of prod member 34 can be appreciated from a comparison of FIGS. 10 and 11.

After the prod member is moved to its outwardly extending position, the safety cap member 100 can be telescopically placed over the forward portion of the forward housing member 14. More particularly, the forward annular flange 104 of the cap member is sized to be able to snap into place within an annular groove 136 disposed in the exterior surface of the forward housing member 14, towards the forward end thereof. The cap member can thus be retained in a protective position covering the forwardmost end of the prod member 34. This latter movement of the safety cap member 100 simulates the manner in which the safety cap member is to be placed over a projecting needle of an automatic injector extending forwardly from the outer structure 12 to prevent accidental or unwanted contact with a needle after an actual injection operation.

In the preferred embodiment, each of the elements comprising the training device of the present invention, with the exception of coil spring 44, is formed from a molded plastic material. The slight, flexible nature of the plastic material enables the entire assembly to be easily snapped together in a manufacturing operation.

It thus will be seen that the objects of this invention have been fully and effectively accomplished. It will be realized, however, that the foregoing preferred specific embodiment has been shown and described for the purpose of this invention and is subject to change without departure from such principles. Therefore, this invention includes all modifications encompassed within the spirit and scope of the following claims.

What is claimed is:

1. An automatic injector training device comprising:
    an outer structure having i) a rearward end, ii) a forward end arranged to be engaged with an injection site of the user, and iii) an intermediate generally cylindrical portion disposed between said forward and rearward ends and constructed and arranged to be manually gripped by the user;
    a movable manually engageable member extending outwardly from the rearward end of the outer structure and adapted to be manually engaged and depressed by the user while said intermediate portion is being gripped by the user, said engageable member being movable between a storage position and an activated position by being manually depressed by the user;
    a prod member movable within said outer structure between a retracted position wherein a forward portion thereof is disposed retracted within the outer structure and an outwardly extending position wherein said forward portion thereof extends outwardly from the forward end of the outer structure, said prod member being movable from said retracted position to said outwardly extending position when said engageable member is manually moved from said storage position to said activated position and being movable from said outwardly extending position to said retracted position when said engageable member is manually moved from said activated position to said storage position;
    a spring member disposed within said outer structure and arranged so as to tend to bias said prod member rearwardly within said outer structure to thus move said prod member from said outwardly extending position to said retracted position when the engageable member is moved from the activated position to the storage position, said engageable member being disposed so that manual movement thereof from said storage position to said activated position moves said prod member against the bias of said spring member so that said forward end of the prod member is moved to extend outwardly from the forward end of the outer structure;
    releasable locking elements disposed within said outer structure constructed and arranged to retain said prod member in said outwardly extending position when said engageable member is moved from the storage position to the activated position and to permit said prod member to be moved by said spring member from said outwardly extending position to said retracted position when said engageable member is moved from the activated position to the storage position; and
    a safety member constructed and arranged to be movable between a safety position wherein the safety member prevents manual movement of said engageable member and a non-safety position which permits the engageable member to be manually moved between said activated position and said storage position.

2. An automatic injector training device according to claim 1, wherein said safety member is constructed and arranged to be able to cooperate with said outer structure so as to be able to be secured to the outer structure and cover the forward portion of the prod member after said safety member is moved to the non-safety position so as to prevent manual contact with the forward portion of the prod member.

* * * * *

UNITED STATES PATENT AND TRADEMARK OFFICE
CERTIFICATE OF CORRECTION

PATENT NO.  : 5,567,160

DATED       : October 26, 1995

INVENTOR(S) : MASSINO, Frank

It is certified that error appears in the above-identified patent and that said Letters Patent is hereby corrected as shown below:

Column 5, line 15, change "six" to --three--.

Signed and Sealed this

Seventeenth Day of February, 1998

Attest:

BRUCE LEHMAN

*Attesting Officer*          *Commissioner of Patents and Trademarks*